(12) United States Patent
Yamashita et al.

(10) Patent No.: US 6,858,849 B2
(45) Date of Patent: Feb. 22, 2005

(54) PET APPARATUS

(75) Inventors: Takaji Yamashita, Hamamatsu (JP); Hiroyuki Okada, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 272 days.

(21) Appl. No.: 10/276,975

(22) PCT Filed: May 22, 2001

(86) PCT No.: PCT/JP01/04281
§ 371 (c)(1),
(2), (4) Date: Nov. 21, 2002

(87) PCT Pub. No.: WO01/90779
PCT Pub. Date: Nov. 29, 2001

(65) Prior Publication Data
US 2003/0107000 A1 Jun. 12, 2003

(51) Int. Cl.$^7$ .............................................. G01T 1/164
(52) U.S. Cl. ............................................... 250/363.03
(58) Field of Search ................................... 250/363.03

(56) References Cited

U.S. PATENT DOCUMENTS 4,352,018 A * 9/1982 Tanaka et al. .......... 250/363.03
5,291,021 A * 3/1994 Tanaka et al. .......... 250/363.03
6,175,116 B1 * 1/2001 Gagnon et al. ......... 250/363.03
6,211,523 B1 * 4/2001 Gagnon .................. 250/363.04
6,249,003 B1 * 6/2001 Culp ...................... 250/363.04

FOREIGN PATENT DOCUMENTS

JP          63-075587        5/1988
JP           7-198853        1/1995

* cited by examiner

*Primary Examiner*—David Porta
*Assistant Examiner*—Marcus Taningco
(74) *Attorney, Agent, or Firm*—Morgan, Lewis & Bockius LLP

(57) ABSTRACT

A PET apparatus (1) includes a detecting section (10). Each cylindrical detector ($13_n$) of the detecting section (10) has a plurality of block detectors ($14_1$ to $14_M$) arranged on the same circumference on a place perpendicular to a central axis (CAX) in the form of a ring. Each block detector ($14_m$) is a two-dimensional position detector which detects the two-dimensional incident position of a photon incident on a light-receiving surface $15b$. Each slice collimator ($21_n$) extends to a rear portion of a corresponding one of cylindrical detectors ($13_n$) through the space between adjacent cylindrical detectors ($13_n$) and ($13_{n+1}$) and is integrally fixed by a holding plate (22) at the rear portion.

21 Claims, 8 Drawing Sheets

PET APPARATUS

TECHNICAL FIELD

The present invention relates to a PET apparatus which can image the behavior of a substance marked by a positron emission isotope (RI radiation source).

BACKGROUND ART

A PET (Positron Emission Tomography) apparatus is an apparatus which can image the behavior of a trace substance in an object (living body) to be examined by detecting a pair of 511 keV photons (gamma rays) which fly in opposite directions upon electron-positron pair annihilation in the object irradiated with RI radiation. The PET apparatus includes a detecting section having many small photon detectors arrayed around a measurement space in which an object to be examined is placed. This apparatus detects a photon pair generated upon electron-positron pair annihilation by coincidence counting, accumulates the coincidence counting information, and reconstructs an image representing the spatial distribution of occurrence frequencies of photon pairs in the measurement space on the basis of these many pieces of accumulated coincidence counting information. This PET apparatus serves an important role in the field of nuclear medicine and the like. For example, biofunctions and the high-order brain functions can be studied by using this apparatus. Such PET apparatuses are roughly classified into two-dimensional PET apparatuses and three-dimensional PET apparatuses.

FIG. 7 is a view for explaining the arrangement of the detecting section of a two-dimensional PET apparatus. FIG. 7 shows an example of an arrangement including seven detector rings, and is a sectional view of the detecting section taken along a plane including the central axis. A detecting section 10 of the two-dimensional PET apparatus has detector rings $R_1$ to $R_7$ stacked between a shield collimator 11 and a shield collimator 12. Each of the detector rings $R_1$ to $R_7$ has a plurality of photon detectors arranged in the form of a ring on a plane perpendicular to the central axis. Each photon detector is a scintillation detector formed from a combination of a scintillator such as BGO ($Bi_4Ge_3O_{12}$) and a photomultiplier. This detector detects photons flying from a measurement space including the central axis. The two-dimensional PET apparatus has slice collimators $S_1$ to $S_6$ inside the detecting section 10. These slice collimators $S_1$ to $S_6$ are ring-like members each of which is placed between adjacent detector rings in a direction parallel to the central axis. Each slice collimator is made of a material having a larger atomic number and larger specific gravity (e.g., lead or tungsten) and has a collimating function of shielding obliquely incident photons (gamma rays).

The detecting section 10 of the two-dimensional PET apparatus having the above arrangement can perform coincidence counting of only a photon pair flying from the nearly 90° direction with respect to the central axis owing to the collimating function of the slice collimators $S_1$ to $S_6$. That is, the coincidence counting information, i.e., two-dimensional projection data, accumulated by the detecting section 10 of the two-dimensional PET apparatus is limited to that obtained by a pair of photon detectors included in a single detector ring or detector rings which are adjacent to each other (or very close to each other). The two-dimensional PET apparatus can therefore efficiently remove scattered radiation produced when a photon pair generated outside the measurement space is scattered. In addition, this apparatus can easily perform absorption correction and sensitivity correction with respect to two-dimensional projection data, and hence can obtain a reconstructed image with good quantitativeness.

FIG. 8 is a view for explaining the arrangement of the detecting section of the three-dimensional PET apparatus. FIG. 8 is also a sectional view of the detecting section taken along a plane including the central axis. The arrangement of the detecting section 10 of the three-dimensional PET apparatus is the same as that of the two-dimensional PET apparatus except that the three-dimensional PET apparatus has no slice collimators. The detecting section 10 of the three-dimensional PET apparatus having this arrangement has a wide solid angle and can perform coincidence counting of a photon pair flying from a wide range as compared with the two-dimensional PET apparatus. That is, as the coincidence counting information, i.e., three-dimensional projection data, obtained and accumulated by the detecting section 10 of the three-dimensional PET apparatus, data obtained by a pair of photon detectors included in an arbitrary detector ring can be used. Three-dimensional PET apparatus can therefore perform coincidence counting of a photon pair with sensitivity five to ten times higher than that of the two-dimensional PET apparatus. As compared with the two-dimensional PET apparatus, however, the three-dimensional PET apparatus has difficulty in accurately removing the influence of scattered radiation, and hence the quantitativeness of a reconstructed image is poor.

As described above, as compared with the three-dimensional PET apparatus, the two-dimensional PET apparatus having slice collimators has low photon pair detection sensitivity but can efficiently remove scattered radiation and easily perform absorption correction and sensitivity correction. The two-dimensional PET apparatus therefore has the merit of obtaining a reconstructed image with excellent quantitativeness.

DISCLOSURE OF INVENTION

However, the present inventor has found the following problems in the above two-dimensional PET apparatus. In the two-dimensional PET apparatus, the slice collimators $S_1$ to $S_6$ exist only inside the detecting section 10 (between the measurement space and the detecting section 10) and are fixed to each other inside the detecting section 10 by a holding plate. In the two-dimensional PET apparatus, it is important to ensure the relative positional relationship between detector rings $R_n$ and slice collimators $S_n$ of the detecting section 10 such that they are alternately arranged in a direction parallel to the central axis. If the precision of the relative positional relationship between the detector rings $R_n$ and the slice collimators $S_n$ is poor, the slice collimator $S_n$ may be located in front of the light-receiving surface of the detector ring $R_n$, resulting in a decrease in the incidence efficiency of photons on each detector ring $R_n$. This causes a deterioration in the performance of the two-dimensional PET apparatus. In order to ensure this relative positional precision, process accuracy and assembly accuracy for the respective detector rings $R_n$, the respective slice collimators $S_n$, and the like must be strictly managed. This makes it difficult to manufacture this apparatus. This leads to an increase in the cost of the two-dimensional PET apparatus.

In addition, in the two-dimensional PET apparatus, since the holding plate for fixing the slice collimators $S_1$ to $S_6$ to each other is placed inside the detecting section 10, photons generated in the measurement space are absorbed by the holding plate, resulting in a decrease in the photon detection sensitivity of the detecting section 10. In general, the holding plate is required to have high mechanical strength to hold the respective slice collimators $S_n$ made of a material having a larger atomic number and larger specific gravity. The holding plate is also required to absorb a small amount of photons. For this reason, for example, a high-strength resin such as a carbon fiber resin or an aluminum alloy is used for the holding plate. In addition, this plate needs to have a thickness of about 6 mm to 10 mm in consideration of a relationship with strength. When aluminum exhibiting a radiation attenuation coefficient of 0.2269/cm with respect to photons (gamma rays) is used for the holding plate, photons are absorbed by the holding plate by about 10% to 20%. As described above, in the two-dimensional PET apparatus, photons generated in the measurement space are absorbed by the holding plate, and hence the photon detection sensitivity of the detecting section 10 decreases.

In the two-dimensional PET apparatus, since the holding plate for fixing the slice collimators $S_1$ to $S_6$ to each other exists inside the detecting section 10, there is a limit in brining the respective detector rings $R_n$ close to the respective slice collimators $S_n$, and a predetermined distance is required between them in the radial direction. For this reason, although a photon passing through between the slice collimator $S_{n-1}$ and the slice collimator $S_n$ should strike the detector ring $R_n$, it may strike the adjacent detector ring $R_{n-1}$ or $R_{n+1}$. This decreases the reliability of accumulated coincidence counting information and affects the quality of a reconstructed image.

In addition, the present inventor has found that the above two- and three-dimensional PET apparatuses have the following problems. Both the two- and three-dimensional PET apparatuses are required to improve the resolution of a reconstructed image. In order to improve the resolution, it is dispensable to reduce the size of each photon detector.

In the case of the two-dimensional PET apparatus, however, as the size of each photon detector decreases, the intervals between the respective slice collimators decrease, resulting in a decrease in open area ratio. This causes a deterioration in photon pair detection sensitivity. With regard to this problem, in the two-dimensional PET apparatus, a decrease in open area ratio can be suppressed by thinning and shortening each slice collimator in accordance with a reduction in the size of each photon detector. However, the effect of shielding photons (gamma rays), i.e., the collimating effect, deteriorates. This makes it impossible to efficiently remove scattered radiation, resulting in a deterioration in the quantitativeness of a reconstructed image.

In the case of the three-dimensional PET apparatus, even if the size of each photon detector is reduced, since no slice collimator is used, a reduction in open area ratio and a deterioration in photon pair detection sensitivity do not occur. As described above, however, in the three-dimensional PET apparatus, since it is essentially difficult to remove the influence of scattered radiation, the quantitativeness of a reconstructed image is poor.

It is an object of the present invention to provide a PET apparatus which can improve photon detection sensitivity.

A PET apparatus according to one aspect of the present invention is characterized by comprising (1) a detecting section which includes a plurality of cylindrical detectors each formed by one- or two-dimensionally arraying a plurality of photon detection elements, each of which detects a photon flying from a measurement space including a central axis, on a cylinder surrounding the central axis, the plurality of cylindrical detectors being arrayed in a direction parallel to the central axis, (2) a plurality of slice collimators which are alternately arranged with the cylindrical detectors in a direction parallel to the central axis, each of the slice collimators extending from a position between the measurement space and the detecting section to a rear portion of a corresponding one of the cylindrical detectors through a space between two adjacent cylindrical detectors of the plurality of cylindrical detectors and passing only a photon, of photons flying from the measurement space, which is substantially parallel to a predetermined plane perpendicular to the central axis toward the detecting section, (3) a coincidence counting information accumulating section which accumulates coincidence counting information of a photon pair detected by one pair of photon detection elements included in the detecting section, and (4) an image reconstructing section which reconstructs an image representing a spatial distribution of occurrence frequencies of photon pairs in the measurement space on the basis of the coincidence counting information accumulated by the coincidence counting information accumulating section.

In the PET apparatus according to the above aspect of the present invention, a photon pair, of photon pairs generated in the measurement space, which has reached the detecting section without being shielded by the slice collimator is simultaneously detected by one pair of photon detection elements included in the detecting section, and the coincidence counting information is converted into information in a coordinate system fixed to the object and accumulated by the coincidence counting information accumulating section. When the accumulation of coincidence counting information by the coincidence counting information accumulating section is terminated, the image reconstructing section reconstructs an image representing the spatial distribution of occurrence frequencies of photon pairs in the measurement space on the basis of the accumulated coincidence counting information.

In the PET apparatus according to the above aspect of the present invention, in particular, the plurality of slice collimators are alternately arranged with the cylindrical detectors in a direction parallel to the central axis, and each slice collimator extends from a position between the measurement space and the detecting section to the rear portion of a corresponding one of the cylindrical detectors through the space between two adjacent cylindrical detectors. The respective slice collimators are then fixed to each other at the rear portions. In the PET apparatus according to the above aspect of the present invention, therefore, the precision of the relative positional relationship between the respective cylindrical detectors and the respective slice collimators is high, and the respective cylindrical detectors and the respective slice collimators are always alternately located in a direction parallel to the central axis. This ensures high incidence efficiency of photons on each cylindrical detector and sufficiently high performance. In addition, since there is no need to strictly manage process accuracy and assembly accuracy for the respective cylindrical detectors, slice collimators, holding plate, and the like, the apparatus can be easily manufactured at low cost.

If the holding plate for fixing the respective slice collimators to each other is placed at the rear portion of the detecting section, photons generated in the measurement space do not pass through the holding plate and are not absorbed by the holding plate. This prevents a decrease in the photon detection sensitivity of the detecting section. In addition, each slice collimator extends to the rear portion of a corresponding one of the cylindrical detectors through the space between two adjacent cylindrical detectors and is fixed by the holding plate at the rear portion. Photons passing through between two adjacent slice collimators always strike the cylindrical detector between the two slice collimators but do not strike the adjacent cylindrical detectors. Therefore, the reliability of accumulated coincidence counting information is high, and the quality of a reconstructed image is excellent.

The PET apparatus according to the above aspect of the present invention is characterized in that the cylindrical detector is formed by arraying a plurality of two-dimensional position detectors, each of which detects a two-dimensional position of a light-receiving surface when a photon is incident thereon, on the predetermined plane in the form of a ring. In this case, this arrangement is suitable to improve the resolution of a reconstructed image by reducing the size of each photon detection element. In this case, each cylindrical detector is designed such that a plurality of detector rings (each corresponding to one layer of photon detectors arrayed in the form of a ring in a direction parallel to the central axis) are stacked. Therefore, detection of coincidence counting information may be performed by a pair of photon detection elements in a single cylindrical detector included in the detecting section, or a pair of photon detection elements respectively included in two adjacent cylindrical detectors depending on the sizes of each cylindrical detector and each slice collimator, or a pair of photon detection elements included in two separate cylindrical detectors. In other words, detection of coincidence counting information may be performed between two adjacent detector rings or between two separate detector rings as well as within the single detector ring. That is, the PET apparatus according to the present invention has an intermediate arrangement between the two-dimensional PET apparatus shown in FIG. 7 and the three-dimensional PET apparatus shown in FIG. 8, and has sensitivity about several times higher than that of the conventional two-dimensional PET apparatus. The PET apparatus according to the present invention can therefore ensure good photon pair detection sensitivity and quantitativeness while improving the resolution of a reconstructed image.

A PET apparatus according to another aspect of the present invention comprises a plurality of photon detection elements which detect one photon and the other photon generated upon electron-positron pair annihilation with light-receiving surfaces facing a measurement space, a plurality of block detectors which are formed by two-dimensionally arraying the plurality of photon detection elements and arranged in a direction crossing a direction in which the light-receiving surfaces face, and a plurality of collimators which are located between adjacent block detectors of the plurality of block detectors, extend from between the adjacent block detectors toward the light-receiving surfaces, and guide only the photons flying from a predetermined direction to the plurality of photon detection elements, respectively.

According to the above aspect of the present invention, each of the plurality of collimators is placed between adjacent block detectors of the plurality of block detectors. Therefore, since the precision of the relative positional relationship between the respective block detectors and the respective collimators is high, the photon detection sensitivity can be improved.

According to the above aspect of the present invention, the apparatus further comprises holding means for holding the plurality of collimators, and the plurality of block detectors are located between the measurement space and the holding means. According to this arrangement, since photons generated in the measurement space are not absorbed by the holding means, the photon detection sensitivity of the block detectors does not deteriorate.

A PET apparatus according to still another aspect of the present invention is characterized by comprising (1) a detecting section which includes a plurality of cylindrical detectors each formed by two-dimensionally arraying a plurality of photon detection elements, each of which detects a photon flying from a measurement space including a central axis, on a cylinder surrounding the central axis, the plurality of cylindrical detectors being arrayed in a direction parallel to the central axis, (2) a plurality of slice collimators which are alternately arranged with the cylindrical detectors at least between the measurement space and the detecting section in a direction parallel to the central axis, and pass only photons, of photons flying from the measurement space, which are substantially parallel to a predetermined plane perpendicular to the central axis toward the detecting section, (3) moving means for moving the detecting section and the plurality of slice collimators together relative to an object to be examined which is placed in the measurement space in a direction parallel to the central axis, (4) a coincidence counting information accumulating section which acquires coincidence counting information of a photon pair detected by one pair of photon detection elements included in the detecting section during a period in which the detecting section and the plurality of slice collimators are moved relative to the object by the moving means, converts the coincidence counting information into information in a coordinate system fixed to the object, and accumulates the converted information, and (5) an image reconstructing section which reconstructs an image representing a spatial distribution of occurrence frequencies of photon pairs in the measurement space on the basis of the coincidence counting information accumulated by the coincidence counting information accumulating section.

In the PET apparatus according to the above aspect of the present invention, the detecting section and the plurality of slice collimators are moved together relative to the object placed in the measurement space by the moving means in a direction parallel to the central axis, and a photon pair, of photon pairs generated in the measurement space, which has reached the detecting section without being shielded by the slice collimator are simultaneously detected by one pair of photon detectors included in the detecting section. The resultant coincidence counting information is converted into information in a coordinate system fixed to the object and accumulated by the coincidence counting information accumulating section. When accumulation of coincidence counting information by the coincidence counting information accumulating section is completed, the image reconstructing section reconstructs an image representing the spatial distribution of occurrence frequencies of photon pairs in the measurement space on the basis of the accumulated coincidence counting information.

In the PET apparatus according to the above aspect of the present invention, detection of coincidence counting information may be performed by a pair of photon detectors in a single cylindrical detector included in the detecting section, or a pair of photon detectors respectively included in two adjacent cylindrical detectors depending on the sizes of each cylindrical detector and each slice collimator, or a pair of photon detectors included in two separate cylindrical detectors. In other words, detection of coincidence counting information may be performed between two adjacent detector rings or between two separate detector rings as well as within the single detector ring (one layer of photon detectors arrayed in the form of a ring in a direction parallel to the central axis). That is, the PET apparatus according to still another aspect of the present invention has an intermediate arrangement between the two-dimensional PET apparatus shown in FIG. 7 and the three-dimensional PET apparatus shown in FIG. 8, and has sensitivity about several times higher than that of the conventional two-dimensional PET apparatus. The PET apparatus according to still another aspect of the present invention can therefore ensure good photon pair detection sensitivity and quantitativeness while improving the resolution of a reconstructed image.

In the PET apparatus according to the above aspect of the present invention, coincidence counting information is accumulated by the coincidence counting information accumulating section during a period in which the detecting section and slice collimators are moved together relative to the object by the moving means in a direction parallel to the central axis. A reconstructed image is then obtained by the image reconstructing section on the basis of the accumulated coincidence counting information. Even with the arrangement in which the cylindrical detectors and slice collimators are alternately arranged, photon pairs can be detected with uniform sensitivity in the body axis direction of the object, and the quantitativeness of a reconstructed image can be made uniform.

A PET apparatus according to still another aspect of the present invention comprises a plurality of photon detection elements which detect one photon and the other photon generated upon electron-positron pair annihilation with light-receiving surfaces facing a measurement space, a plurality of block detectors which are formed by two-dimensionally arraying the plurality of photon detection elements and arranged in a direction crossing a direction in which the light-receiving surfaces face, a plurality of collimators which guide only the photons flying from a predetermined direction to the plurality of photon detection elements, respectively, a coincidence counting information accumulating section which accumulates, when one pair of photon detection elements included in the plurality of block detectors simultaneously detect a photon pair, coincidence counting information of the photon pair detected by the one pair of photon detection elements during a period in which measurement is performed while the plurality of block detectors and the plurality of collimators are relatively moved together, and an image reconstructing section which reconstructs an image representing a spatial distribution of occurrence frequencies of photon pairs in the measurement space on the basis of the coincidence counting information accumulated by the coincidence counting information accumulating section.

In the PET apparatus according to the above aspect of the present invention, coincidence counting information is accumulated by the coincidence counting information accumulating section during a period in which the plurality of block detectors and the plurality of collimators are moved together relative to the object. A reconstructed image is then obtained by the image reconstructing section on the basis of the accumulated coincidence counting information. Photon pairs can be detected with uniform sensitivity in the body axis direction of the object, and the quantitativeness of a reconstructed image can be made uniform.

BEST MODES OF CARRYING OUT THE INVENTION

Figure 1:
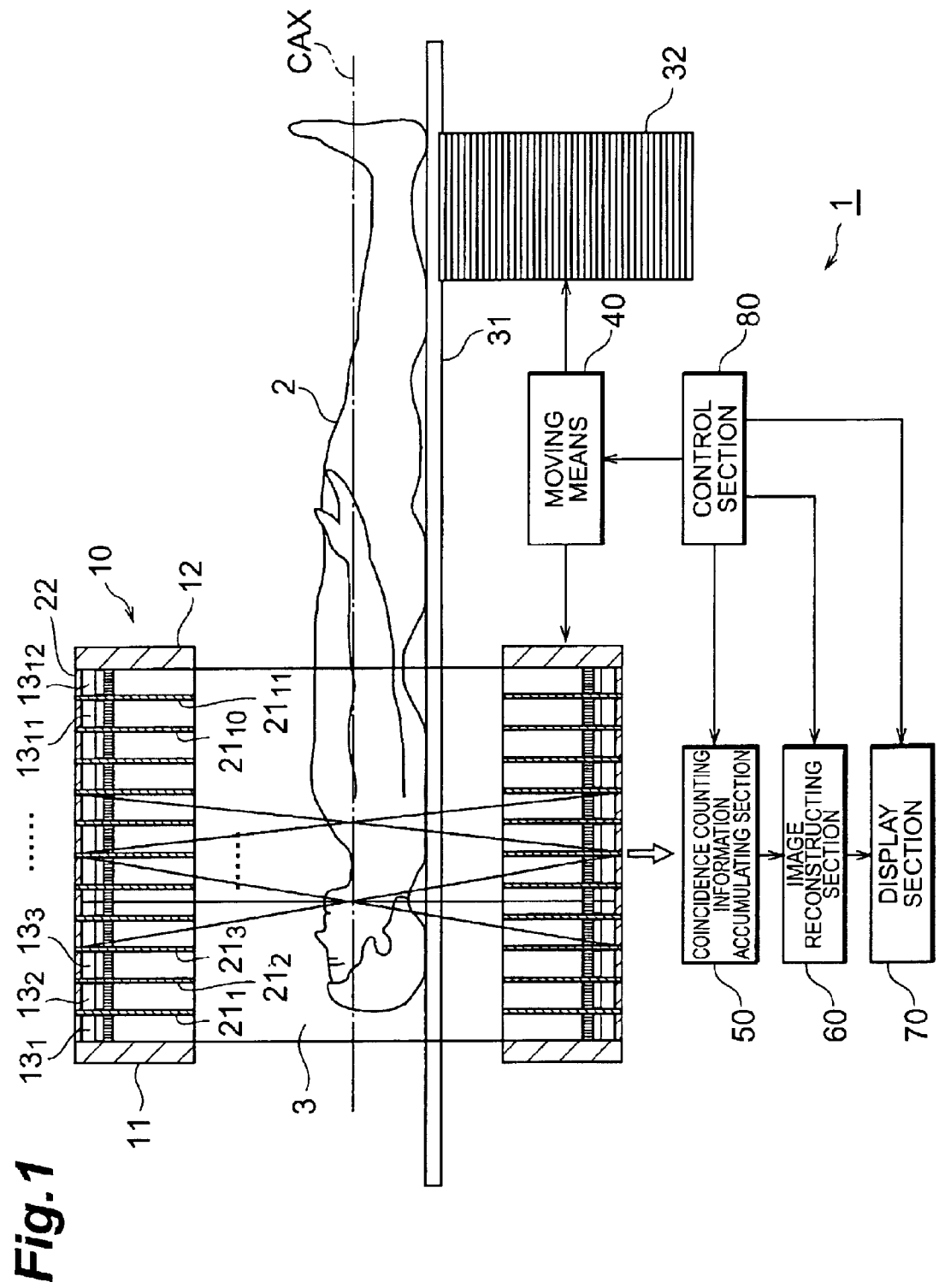
FIG. 1 is a schematic view showing the overall arrangement of a PET apparatus according to the embodiment.

An embodiment of the present invention will be described in detail below with reference to the accompanying drawings. Note that the same reference numerals denote the same elements throughout the drawings, and a repetitive description will be avoided. It is an object of this embodiment to provide an inexpensive PET apparatus which has high photon detection sensitivity, can accumulate highly reliable coincidence counting information, and can be easily manufactured. It is another object of the embodiment to provide a PET apparatus which can ensure good photon pair detection sensitivity and quantitativeness while improving the resolution of a reconstructed image.

FIG. 1 is a view showing the schematic arrangement of the PET apparatus 1 according to this embodiment. FIG. 1 shows cross-sections of a detecting section 10 and slice collimators 21 taken along a plane including a central axis CAX. The PET apparatus 1 according to the embodiment includes the detecting section 10, slice collimators $21_1$ to $21_{11}$, a bed 31, a support base 32, a moving means 40, a coincidence counting information accumulating section 50, an image reconstructing section 60, and a display section 70. FIG. 1 also shows an object 2 to be examined which is an examination target for the PET apparatus 1. In addition, a space where the coincidence counting information of photon pairs can be detected by the PET apparatus 1 is shown as a measurement space 3.

The detecting section 10 has cylindrical detectors $13_1$ to $13_{12}$ arranged in a direction parallel to the central axis CAX between ring-like shield collimators 11 and 12. Each cylindrical detector $13_n$ is designed such that a plurality of photon detectors for respectively detecting photons flying from the measurement space 3 including the central axis CAX are two-dimensionally arranged on a cylinder surrounding the central axis CAX. That is, each cylindrical detector $13_n$ is equivalent to a unit formed by stacking a plurality of detector rings, each formed by arranging a plurality of photon detectors in form of a ring on a plane perpendicular to the central axis CAX, in a direction parallel to the central axis CAX. Each of the slice collimators $21_1$ to $21_{11}$ is an example of a collimator. The slice collimators $21_1$ to $21_{11}$ are alternately arranged on the cylindrical detectors $13_1$ to $13_{12}$ in a direction parallel to the central axis CAX at least between the measurement space 3 and the detecting section 10 to pass only photons, of the photons flying from the measurement space 3, which are substantially parallel to a predetermined plane toward the detecting section 10. The detecting section 10 and slice collimators $21_1$ to $21_{11}$ will be described in detail later.

The bed 31 is used to place the object 2 thereon, and supported by the support base 32. The moving means 40 moves the detecting section 10 and slice collimators $21_1$ to $21_{11}$ together relative to the object 2 placed in the measurement space 3 in a direction parallel to the central axis CAX. This movement is an example of the operation of relatively moving the plurality of block detectors and the plurality of collimators together in a direction crossing the direction in which the light-receiving surfaces face. More specifically, the moving means 40 may move the detecting section 10 and slice collimators $21_1$ to $21_{11}$ together in a direction parallel to the central axis CAX or may move the bed 31 (i.e., the object 2) in a direction parallel to the central axis CAX. In addition, the moving means 40 may move them in only one direction during measurement or reciprocate them. Relative movement is done by the moving means 40 such that the region of interest of the object 2 is moved by a distance equal to or more than ½ the arrangement pitch of the respective cylindrical detectors $13_n$ during measurement. Preferably, the region of interest of the object 2 is relatively moved at a constant speed in the measurement space 3 by a distance corresponding to an integer multiple of the above pitch during measurement. If the regions of interest of the object 2 exist over a predetermined range in the central axis CAX direction; it is preferable that each region in the predetermined range stay in the measurement space 3 for an almost constant period of time during measurement.

The coincidence counting information accumulating section 50 accumulates coincidence counting information of photon pairs detected by one pair of photon detectors included in the detecting section 10 during a period in which the detecting section 10 and slice collimators $21_1$ to $21_{11}$ are moved relative to the object 2 by the moving means 40. In accumulating coincidence counting information, the coincidence counting information detected by the detecting section 10 is converted into information in a coordinate system fixed to the object 2 on the basis of the displacement amounts of the slice collimators $21_1$ to $21_{11}$ and detecting section 10 relative to the object 2, and the coincidence counting information having undergone this coordinate conversion is accumulated. Note that as the relative displacement amounts, the data obtained by an encoder or the like or the data recorded by the moving means 40 may be used.

The image reconstructing section 60 reconstructs an image representing the spatial distribution of occurrence frequencies of photon pairs in the measurement space 3 on the basis of the coincidence counting information accumulated by the coincidence counting information accumulating section 50. The image reconstructing section 60 also performs sensitivity correction to correct variations in detection sensitivity of the respective photon detectors of the detecting section 10, absorption correction to correct the absorption of photons in the object 2, and scatter correction to correct scattering of photons in the object 2. The display section 70 displays the reconstructed image obtained by the image reconstructing section 60. A control section 80 controls relative movement done by the moving means 40, accumulation of coincidence counting information by the coincidence counting information accumulating section 50, image reconstruction done by the image reconstructing section 60, and display of a reconstructed image by the display section 70.

Figure 2:
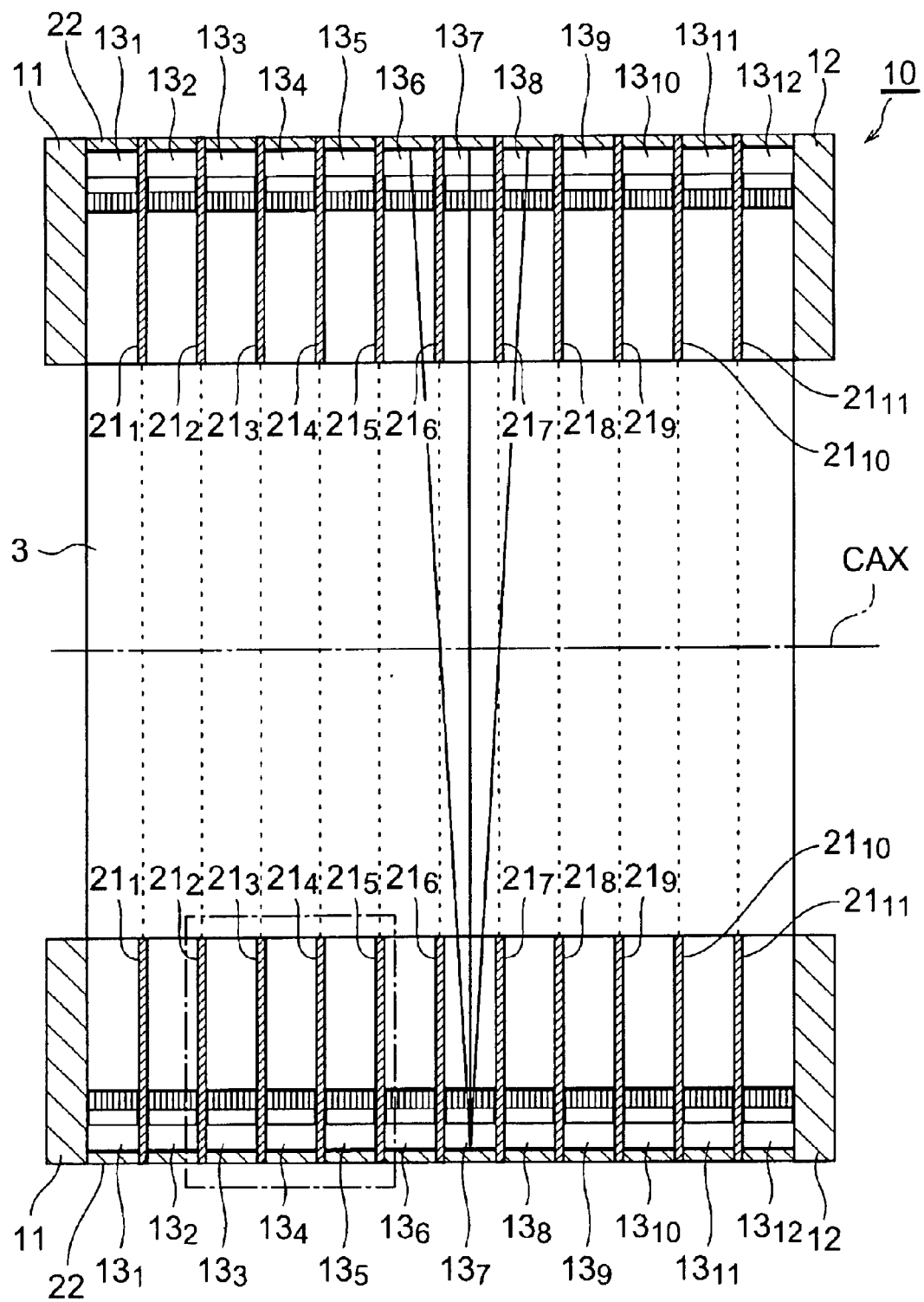
FIG. 2 is a view for explaining the arrangement of the detecting section and slice collimator of the PET apparatus according to this embodiment.

FIG. 2 is a view for explaining the arrangements of the detecting section 10 and slice collimator 21 of the PET apparatus according to this embodiment. FIG. 2 shows cross-sections of the detecting section 10 and slice collimators $21_1$ to $21_{11}$ taken along a plane including the central axis CAX. The detecting section 10 of the PET apparatus according to this embodiment includes the cylindrical detectors $13_1$ to $13_{12}$ stacked in a direction parallel to the central axis CAX between the ring-like shield collimators 11 and 12. The respective ring-like slice collimators $21_1$ to $21_{11}$ are alternately arranged with the cylindrical detectors $13_n$ in a direction parallel to the central axis CAX. That is, each slice collimator $21_n$ is placed between the cylindrical detector $13_n$ and a cylindrical detector $13_{n+1}$ which are adjacent to each other. Each slice collimator $21_n$ is made of a material having a larger atomic number and larger specific gravity (e.g., lead or tungsten) and several mm (e.g., 5 mm to 6 mm) thick. Each slice collimator $21_n$ has a collimating function of passing photons, of photons flying from the measurement space, which are substantially parallel to a plane perpendicular to the central axis CAX toward the detecting section 10 and shielding obliquely incident photons.

Figure 3:
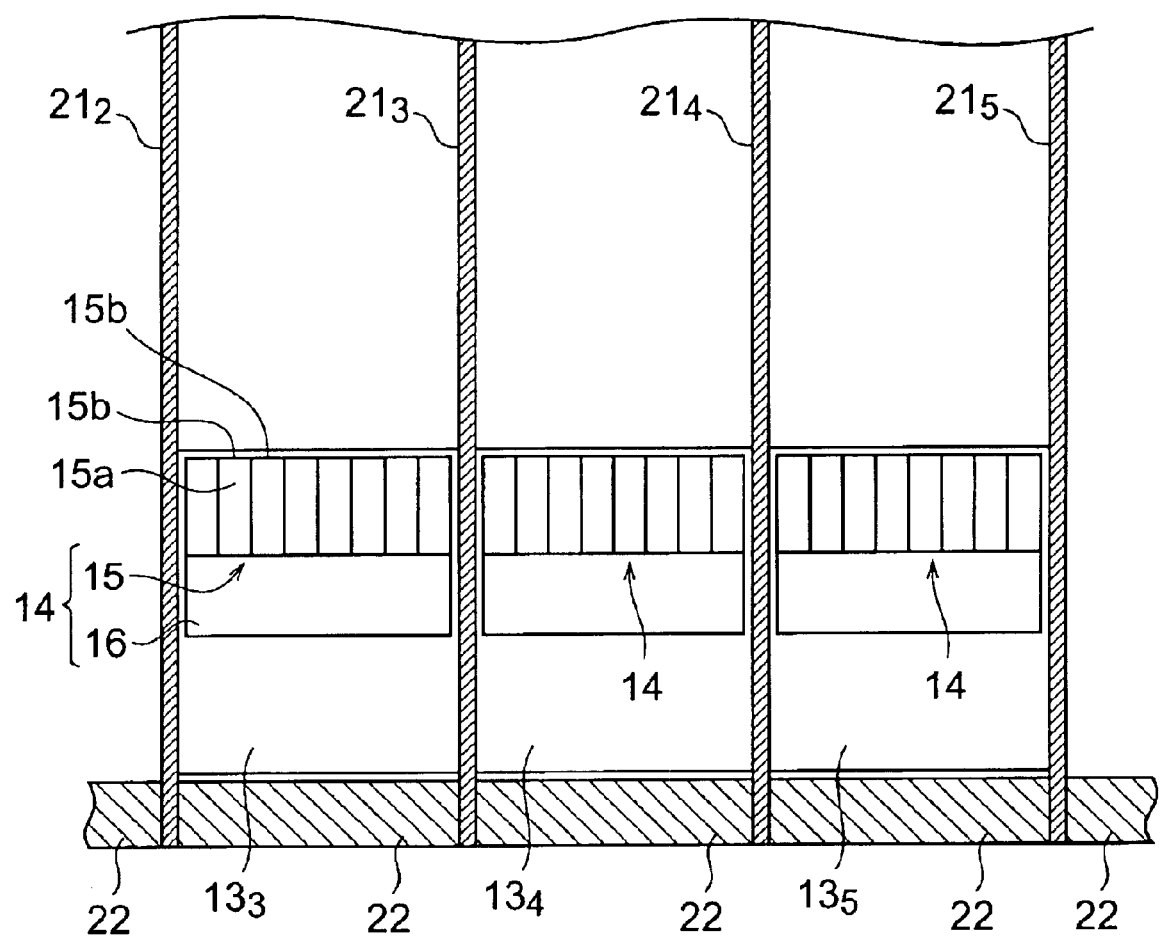
FIG. 3 is an enlarged view partly showing the detecting section and slice collimator of the PET apparatus according to this embodiment.
Figure 4:
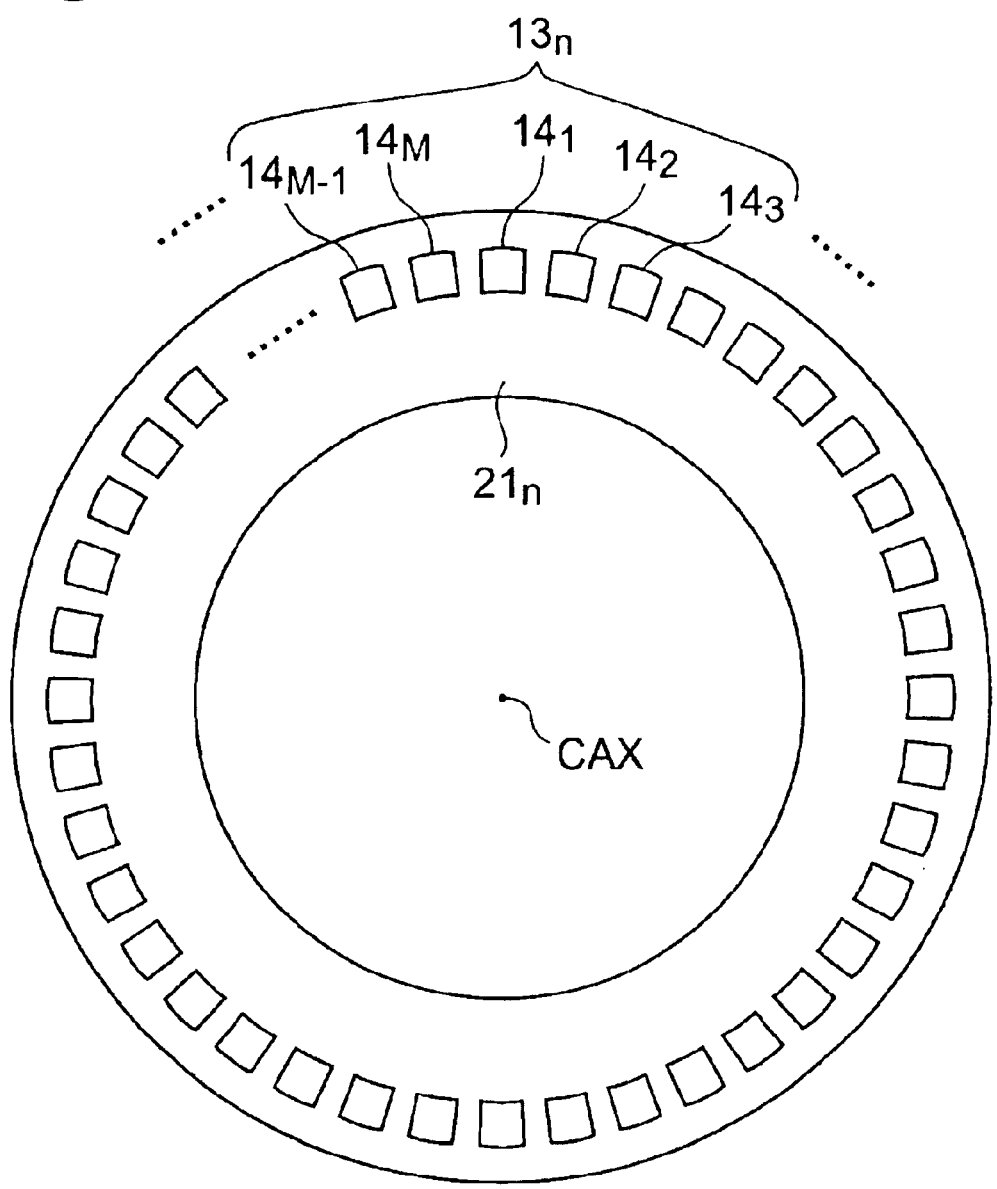
FIG. 4 view for explaining the arrangement of cylindrical detectors and slice collimators of the PET apparatus according to this embodiment.

FIG. 3 is an enlarged view of a portion (the portion enclosed with the chain line in FIG. 2) of the detecting section 10 and slice collimators 21 of the PET apparatus according to this embodiment. FIG. 4 is a view for explaining the arrangement of the cylindrical detector $13_n$ and slice collimator $21_n$ of the PET apparatus according to this embodiment. FIG. 4 shows the relationship between the cylindrical detector $13_n$ and the slice collimator $21_n$ when viewed from a direction parallel to the central axis CAX. Each cylindrical detector $13_n$ has a plurality of block detectors $41_1$ to $14_M$ arranged in the form of a ring on the same circumference on a plane perpendicular to the central axis CAX. Each block detector $14_m$ serves as a two-dimensional position detector for detecting the two-dimensional incident position of a photon incident on an the light-receiving surface 15b. Each slice collimator $21_n$ reaches the rear portion of the corresponding cylindrical detector $13_n$ through the space between the cylindrical detector $13_n$ and the cylindrical detector $13_{n+1}$ which are adjacent to each other and is integrally fixed to a holding plate 22 at the rear portion. The holding plate 22 is an example of a holding means. As shown in FIG. 2, the plurality of block detectors 14 provided for the respective cylindrical detectors $13_n$ are located between the measurement space 3 and the holding plate 22. As shown in FIG. 3, the respective slice collimators $21_n$ are located between the adjacent block detectors 14, extend from between the adjacent block detectors 14 toward the light-receiving surfaces 15b, and guide only photons flying from a predetermined direction toward a plurality of photon detection elements 15a. Each slice collimator $21_n$ extends from between the adjacent block detectors 14 toward the holding plate 22. As shown in FIGS. 3 and 4, the plurality of block detectors $41_1$ to $14_M$ provided for the respective cylindrical detectors $13_n$ are so arranged as to form a cylindrical shape surrounding the measurement space 3.

Figure 5:
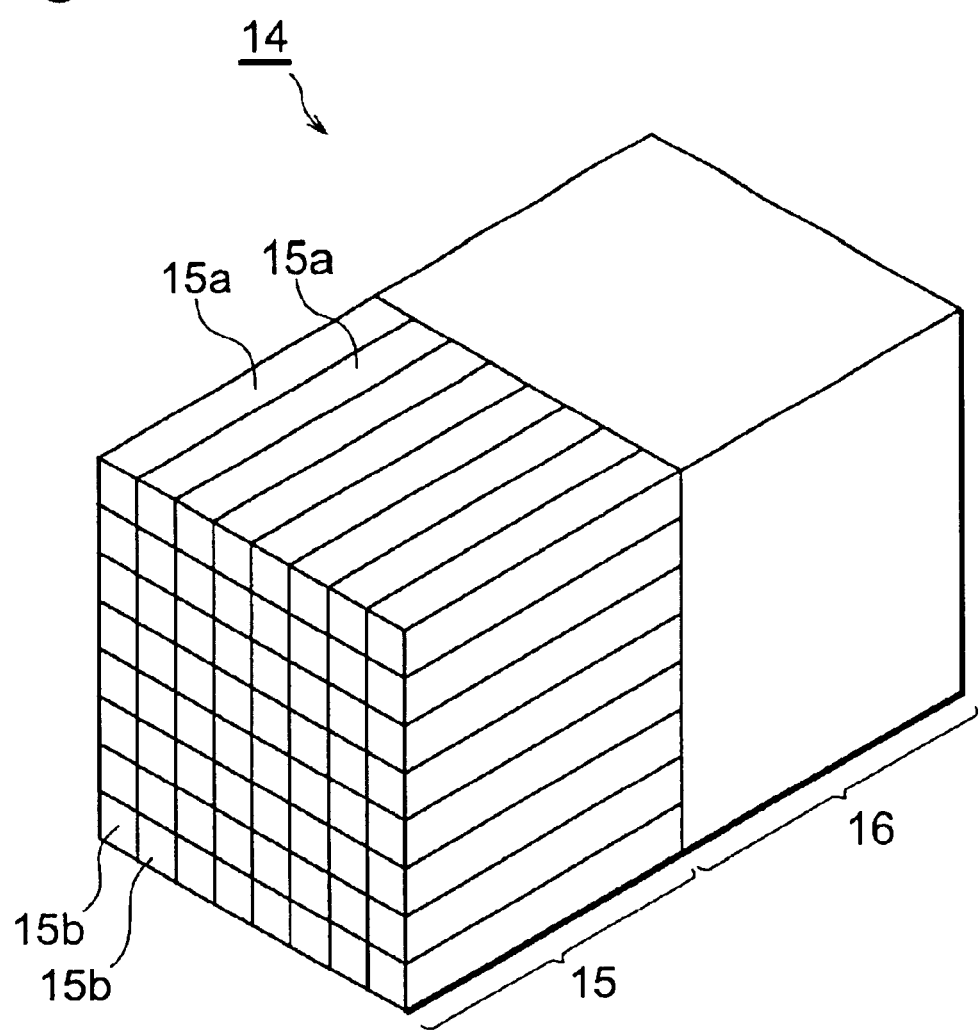
FIG. 5 is a view showing the arrangement of a block detector mounted in the PET apparatus according to this embodiment.

FIG. 5 is a view showing the arrangement of a block detector 14. As shown in FIG. 5, each block detector $14_m$ is a scintillation detector formed from a combination of a scintillation block 15 constituted by P×Q (P≧2, Q≧2) segments, and a position detection type photomultiplier 16. Each block detector $14_m$ detects a photon flying from the measurement space and also detects the two-dimensional incident position of the photon incident on the light-receiving surface 15b of the scintillation block 15. That is, the block detector $14_m$ is equivalent to a unit obtained by two-dimensionally arranging P×Q small photon detectors $15a$. Each cylindrical detector $13_n$ constituted by such block detectors $14_m$ arranged in the form of a ring is equivalent to a unit obtained by stacking a plurality of detector rings, each constituted by a plurality of photon detectors $15a$ arranged in the form of a ring on a plane perpendicular to the central axis CAX, in a direction parallel to the central axis CAX. In the block detector $14_m$, a resistor array for applying a predetermined voltage to each electrode in the position detection type photomultiplier 16 and a preamplifier for receiving the current signal output from the anode electrode of the position detection type photomultiplier 16 and outputting it as a voltage signal are housed in a casing, together with the scintillation block 15 and position detection type photomultiplier 16, for light shielding.

For example, BGO ($Bi_4Ge_3O_{12}$), GSO ($Gd_2SiO_5(Ce)$), LSO ($Lu_2SiO_5(Ce)$), or PWO ($PbWO_4$) is used for the scintillation block 15, as needed. The scintillation block 15 is constituted by 8×8 segments, and each segment has a size of 6 mm×6 mm×20 mm. The area of the photoelectric surface of the position detection type photomultiplier 16 is 50 mm×50 mm. The cylindrical detector $13_n$ is formed by arranging 60 block detectors $14_m$, each including the scintillation block 15 and position detection type photomultiplier 16, in the form of a ring. Each cylindrical detector $13_n$ has an inner diameter of about 1,000 mm. Each slice collimator $21_n$ has an inner diameter of 600 mm. The structure formed by alternately stacking the cylindrical detectors $13_1$ to $13_{12}$ and slice collimators $21_1$ to $21_{11}$ in a direction parallel to the central axis CAX has a thickness (i.e., the visual field in the body axis direction) of about 670 mm.

Under such conditions, detection of a pair of 511 keV photons (gamma rays) generated upon electron-positron pair annihilation in the measurement space 3 and flying in opposite directions, i.e., detection of coincidence counting information, may be performed by a pair of block detectors 14 in the same cylindrical detector $13_n$ or a pair of block detectors 14 respectively included in the adjacent cylindrical detectors $13_n$ and $13_{n+1}$. Detection of coincidence counting information may be performed by a pair of block detectors 14 included in two separate cylindrical detectors 13. In other words, detection of coincidence counting information may be performed between two adjacent detector rings or two separate detector rings as well as within the single detector ring.

Figure 7:
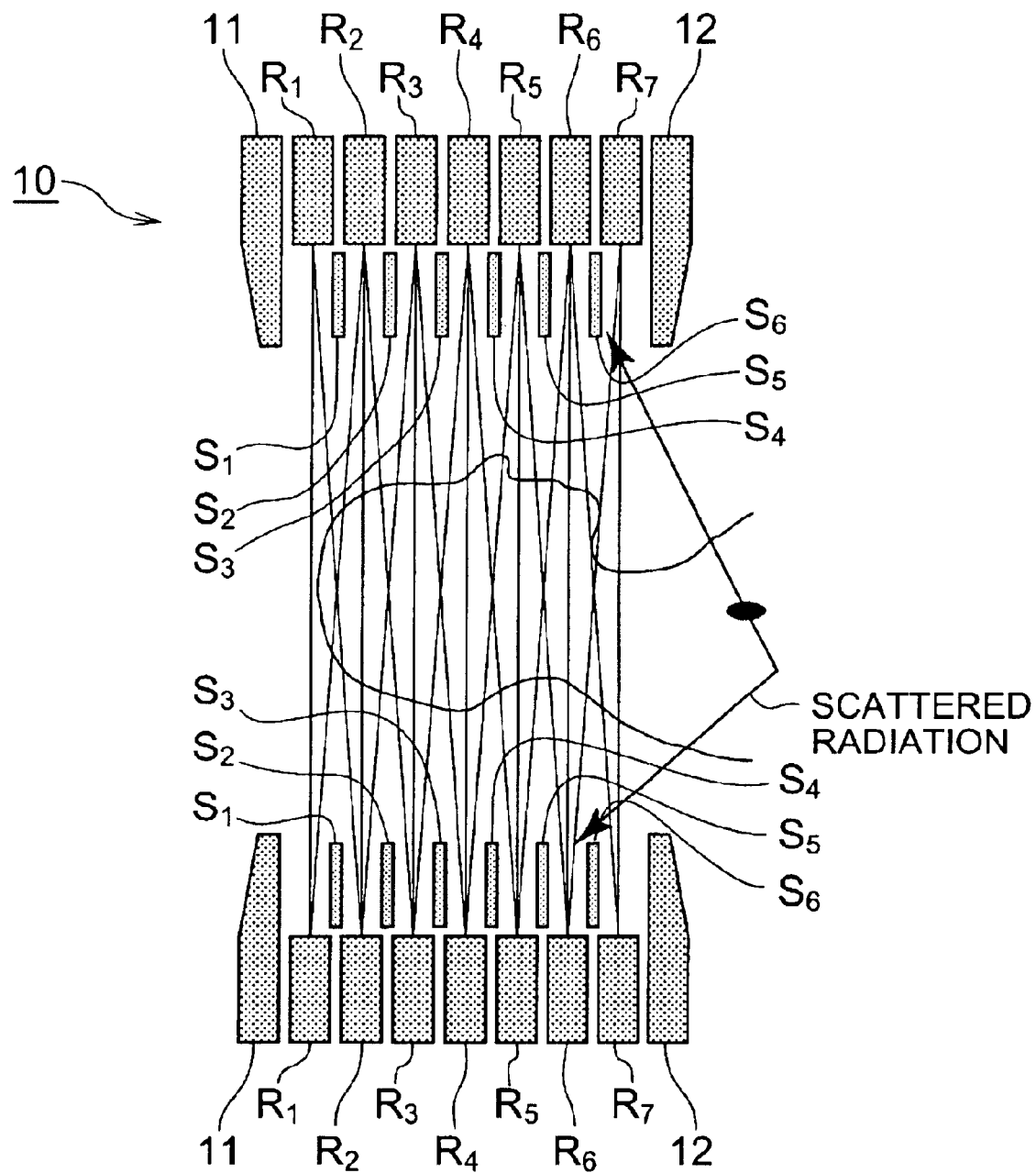
FIG. 7 is a view for explaining the arrangement of a two-dimensional PET apparatus.
Figure 8:
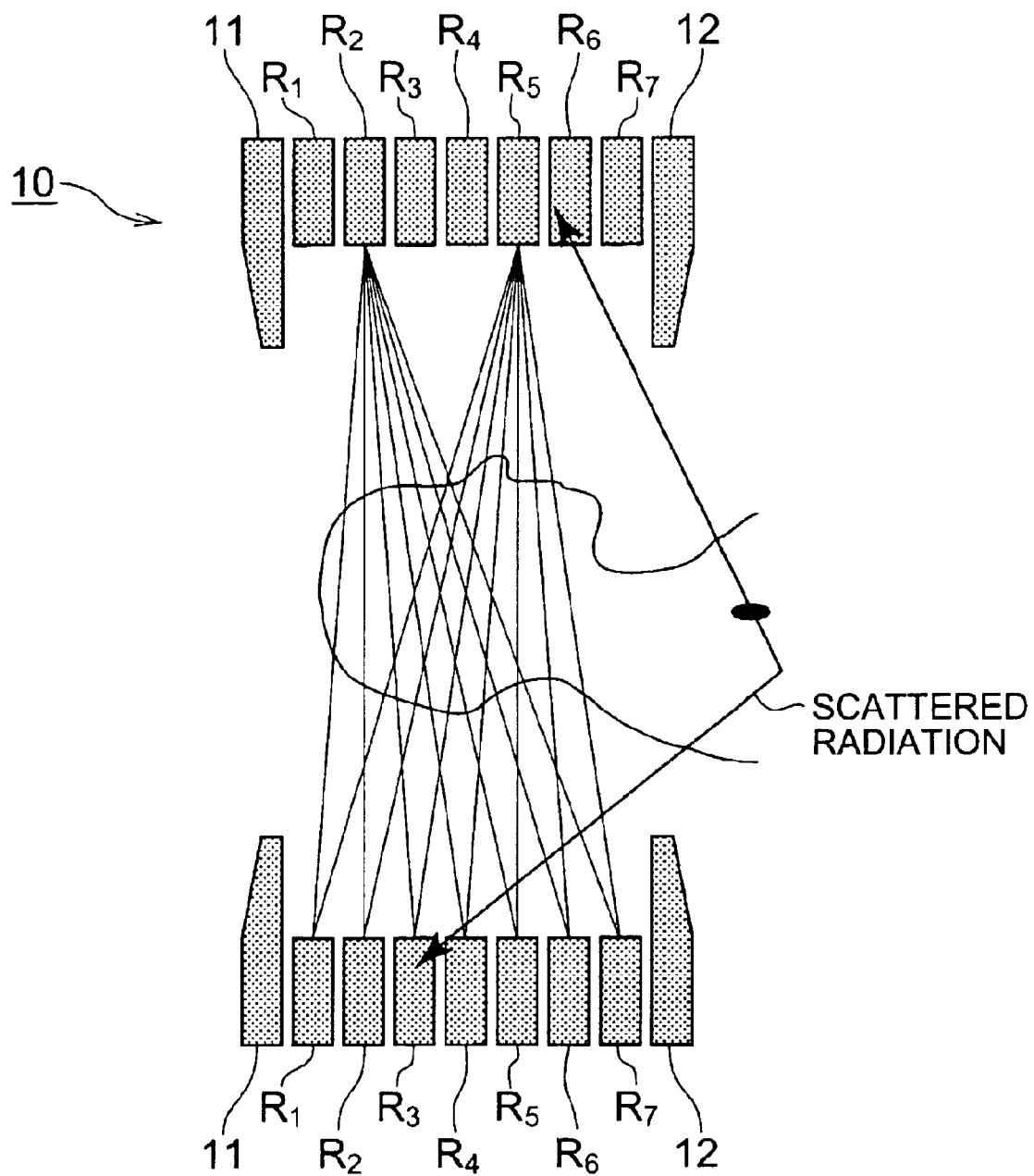
FIG. 8 is a view for explaining the arrangement of a three-dimensional PET apparatus.

That is, the PET apparatus 1 according to this embodiment has an intermediate arrangement between the two-dimensional PET apparatus shown in FIG. 7 and the three-dimensional PET apparatus. shown in FIG. 8 When sensitivity per unit visual field length (cm) in the body axis direction under the above conditions is calculated, the sensitivity of the PET apparatus 1 according to this embodiment is about 1.3 kcps/(kBq·ml), which is about ½ the sensitivity (about 2.58 kcps/(kBq·ml)) of the conventional three-dimensional PET apparatus, but is about four to five times higher than the sensitivity (about 0.28 kcps/(kBq·ml)) of the conventional two-dimensional PET apparatus.

The operation of the PET apparatus 1 according to this embodiment will be described next. The object 2 to which an RI is applied is placed on the bed 31, and the region of interest of the object 2 is positioned in the measurement space 3. The PET apparatus 1 operates in the following manner under the control of the control section 80. First of all, the moving means 40 starts to move the detecting section 10 and slice collimators $21_1$ to $21_{11}$ together relative to the object 2 placed in the measurement space 3 in a direction parallel to the central axis CAX.

Of the 511 keV photons (gamma rays) generated upon electron-positron pair annihilation in the measurement space 3, photons that have reached the detecting section 10 without being shielded by the slice collimators $21_{11}$ to $21_{11}$ are simultaneously detected by one pair of photon detection elements $15a$ included in the detecting section 10. The coincidence counting information simultaneously detected by the detecting section 10 during the period of this relative movement is converted into information in a coordinate system fixed to the object 2 on the basis of the relative displacement amounts of the detecting section 10 and slice collimators $21_1$ to $21_{11}$ with respect to the object 2. The resultant information is accumulated by the coincidence counting information accumulating section 50.

When a predetermined measurement period comes to an end, the coincidence counting information accumulating section 50 stops accumulating coincidence counting information, and the moving means 40 also stops relative movement. The image reconstructing section 60 reconstructs an image representing the spatial distribution of occurrence frequencies of photon pairs in the measurement space 3 on the basis of the coincidence counting information accumulated by the coincidence counting information accumulating section 50. The image reconstructing section 60 also performs sensitivity correction, absorption correction, and scatter correction. The reconstructed image obtained by the image reconstructing section 60 is displayed by the display section 70.

As described above, in the PET apparatus 1 according to this embodiment, the slice collimator $21_n$ reaches the rear portion of each cylindrical detector $13_n$ through the space between the cylindrical detector $13_n$ and the cylindrical detector $13_{n+1}$, and is integrally fixed by the holding plate 22 at the rear portion. In the PET apparatus 1 according to this embodiment, therefore, the precision of relative positional relationship between each cylindrical detector $13_n$ and a corresponding one of the slice collimators $21_n$ is high, and the-respective cylindrical detectors $13_n$ and the respective slice collimators $21_n$ are alternately arranged in a direction parallel to the central axis CAX. This ensures high incidence efficiency of photons on each cylindrical detector $13_n$ and sufficiently high performance. In addition, since there is no need to strictly manage process accuracy and assembly accuracy for the respective cylindrical detectors $13_n$, slice collimators $21_n$, holding plate 22, and the like, the apparatus can be easily manufactured at low cost. Furthermore, this arrangement is suitable to move the detecting section 10 and slice collimators $21_1$ to $21_{11}$ together in a direction parallel to the central axis CAX.

In the PET apparatus 1 according to this embodiment, since the holding plate 22 for fixing the slice collimators $21_n$ to each other is located at the rear portion of the detecting section 10, photons generated in the measurement space 3 do not pass through the holding plate 22 and are not absorbed by the holding plate 22. Therefore, the photon detection sensitivity of the detecting section 10 does not decrease.

In addition, in the PET apparatus 1 according to this embodiment, the slice collimator $21_n$ extends to the rear portion of each cylindrical detector $13_n$ through the space between the cylindrical detector $13_n$ and the cylindrical detector $13_{n+1}$ and is fixed by the holding plate 22 at the rear portion, photons passing through between the slice collimator $S_{n-1}$ and the slice collimator $S_n$ always strike the cylindrical detector $13_n$ but do not strike the adjacent cylindrical detector $13_{n-1}$ or cylindrical detector $13_{n+1}$. Therefore, the reliability of accumulated coincidence counting information is high, and the quality of a reconstructed image is high.

The detecting section 10 of the PET apparatus 1 according to this embodiment has the cylindrical detectors $13_1$ to $13_{12}$ arranged in a direction parallel to the central axis CAX. Each cylindrical detector $13_n$ is designed such that a plurality of photon detection elements 15a are two-dimensionally arranged on a cylinder surrounding the central axis CAX. The cylindrical detectors $13_1$ to $13_{12}$ and slice collimators $21_1$ to $21_{11}$ are alternately arranged in a direction parallel to the central axis CAX. This arrangement of the detecting section 10 makes it possible to improve the resolution of a reconstructed image by reducing the size of each photon detection element 15a. In addition, since the slice collimators $12_n$ are not arranged between the detector rings but are arranged between the cylindrical detectors $13_n$, intervals are ensured between the respective slice collimators $12_n$ to suppress a decrease in open area ratio, thus ensuring high photon pair detection sensitivity. Furthermore, since each slice collimator $12_n$ need not be thinned, the collimating effect can be maintained, and scattered radiation can be efficiently removed. This makes it possible to ensure high quantitativeness of a reconstructed image. As described above, the PET apparatus 1 according to this embodiment can ensure good photon pair detection sensitivity and quantitativeness while improving the resolution of a reconstructed image.

While the detecting section 10 and slice collimators $21_1$ to $21_{11}$ are moved together relative to the object 2 in a direction parallel to the central axis CAX by the moving means 40, coincidence counting information is accumulated by the coincidence counting information accumulating section 50, and a reconstructed image is obtained by the image reconstructing section 60 on the basis of this accumulated coincidence counting information. In this embodiment, therefore, even with the above arrangement of the cylindrical detectors $13_1$ to $13_{12}$ and slice collimators $21_1$ to $21_{11}$, photon pairs can be detected with uniform sensitivity in the body axis direction of the object 2, and the quantitativeness of a reconstructed image can be made uniform.

In addition, in this embodiment, each cylindrical detector $13_n$ is formed from a ring-like array of a plurality of two-dimensional detectors (block detectors $14_m$) which detect the two-dimensional incident positions of photons incident on the light-receiving surfaces 15b. This arrangement is therefore suitable to improve the resolution of a reconstructed image by reducing the size of each photon detection element 15a.

Figure 6:
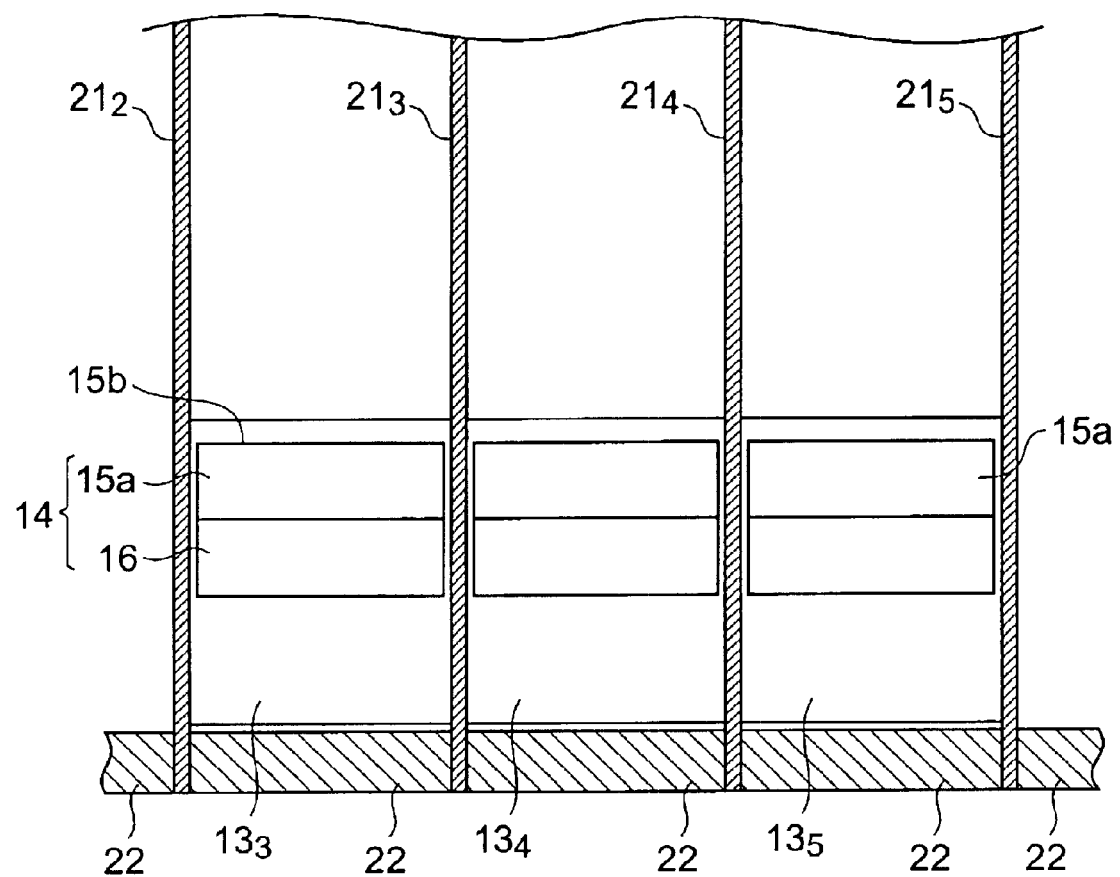
FIG. 6 is an enlarged view partly showing the detecting section and slice collimator of a one-dimensional PET apparatus according to a modification to this embodiment.

The present invention is not limited to the above embodiment and can be variously modified. For example, in the above embodiment, the cylindrical detector $13_n$ located between the adjacent slice collimators $S_{n-1}$ and $S_n$ is designed such that a plurality of photon detection elements 15a are two-dimensionally arrayed on a cylinder surrounding the central axis CAX, and a plurality of detector rings (each corresponding to one layer of photon detection elements 15a arrayed in the form of a ring in a direction parallel to the central axis) are stacked in a direction parallel to the central axis CAX. However, as shown in FIG. 6, each cylindrical detector $13_n$ may be designed such that a plurality of photon detection elements 15a are one-dimensionally arrayed on a cylinder surrounding the central axis CAX (i.e., one layer of detector ring). The same reference numerals as in FIG. 3 denote the same elements in FIG. 6, and a detailed description thereof will be omitted.

INDUSTRIAL APPLICABILITY

As has been described in detail above, according to the PET apparatus of the present invention, the photon detection sensitivity can be increased.

What is claimed is:

1. A PET apparatus comprising:

a detecting section which includes a plurality of cylindrical detectors each formed by one- or two-dimensionally arraying a plurality of photon detection elements, each of which detects a photon flying from a measurement space including a central axis, on a cylinder surrounding the central axis, the plurality of cylindrical detectors being arrayed in a direction parallel to the central axis;

a plurality of slice collimators which are alternately arranged with said cylindrical detectors in a direction parallel to the central axis, each of said slice collimators extending from a position between the measurement space and said detecting section to a rear portion of a corresponding one of the cylindrical detectors through a space between two adjacent cylindrical detectors of the plurality of cylindrical detectors and passing only a photon, of photons flying from the measurement space, which is substantially parallel to a predetermined plane perpendicular to the central axis toward said detecting section;

a coincidence counting information accumulating section which accumulates coincidence counting information of a photon pair detected by one pair of photon detection elements included in said detecting section; and an image reconstructing section which reconstructs an image representing a spatial distribution of occurrence frequencies of photon pairs in the measurement space on the basis of the coincidence counting information accumulated by said coincidence counting information accumulating section.

2. A PET apparatus according to claim 1, wherein said cylindrical detector is formed by arraying a plurality of two-dimensional position detectors, each of which detects a two-dimensional position of a light-receiving surface when a photon is incident thereon, on the predetermined plane in the form of a ring.

3. A PET apparatus comprising:

a plurality of photon detection elements which detect one photon and the other photon generated upon electron-positron pair annihilation with light-receiving surfaces facing a measurement space;

a plurality of block detectors which are formed by two-dimensionally arraying said plurality of photon detection elements and arranged in a direction crossing a direction in which the light-receiving surfaces face; and a plurality of collimators which are located between adjacent block detectors of said plurality of block detectors, extend from between the adjacent block detectors toward the light-receiving surfaces, and guide only the photons flying from a predetermined direction to said plurality of photon detection elements, respectively.

4. A PET apparatus according to claim 3, wherein said apparatus further comprises holding means for holding said plurality of collimators, and said plurality of block detectors are located between the measurement space and said holding means.

5. A PET apparatus according to claim 3, wherein said plurality of collimators extend from between adjacent block detectors of said plurality of block detectors toward said holding means.

6. A PET apparatus according to claim 3, wherein said plurality of block detectors are so arranged as to form a cylindrical shape surrounding the measurement space.

7. A PET apparatus comprising:
a detecting section which includes a plurality of cylindrical detectors each formed by two-dimensionally arraying a plurality of photon detection elements, each of which detects a photon flying from a measurement space including a central axis, on a cylinder surrounding the central axis, the plurality of cylindrical detectors being arrayed in a direction parallel to the central axis;
a plurality of slice collimators which are alternately arranged with said cylindrical detectors at least between the measurement space and said detecting section in a direction parallel to the central axis, and pass only photons, of photons flying from the measurement space, which are substantially parallel to a predetermined plane perpendicular to the central axis toward said detecting section;
moving means for moving said detecting section and said plurality of slice collimators together relative to an object to be examined which is placed in the measurement space in a direction parallel to the central axis;
a coincidence counting information accumulating section which acquires coincidence counting information of a photon pair detected by one pair of photon detection elements included in said detecting section during a period in which said detecting section and said plurality of slice collimators are moved relative to the object by said moving means, converts the coincidence counting information into information in a coordinate system fixed to the object, and accumulates the converted information; and
an image reconstructing section which reconstructs an image representing a spatial distribution of occurrence frequencies of photon pairs in the measurement space on the basis of the coincidence counting information accumulated by said coincidence counting information accumulating section.

8. A PET apparatus according to claim 7, wherein said cylindrical detector is formed by arraying a plurality of two-dimensional position detectors, each of which detects a two-dimensional position of a light-receiving surface when a photon is incident thereon, on the predetermined plane in the form of a ring.

9. A PET apparatus according to claim 7, wherein each of said plurality of slice collimators extends to a rear portion of a corresponding one of said cylindrical detectors through a space between two adjacent cylindrical detector of said plurality of cylindrical detectors included in said detecting section.

10. A PET apparatus according to claim 7, wherein said detecting section and said plurality of slice collimators are moved together in a direction parallel to the central axis by said moving means.

11. A PET apparatus according to claim 7, wherein
said apparatus further comprises a bed placed in the measurement space, on which an object to be examined is placed, and
said bed is moved in a direction parallel to the central axis by said moving means.

12. A PET apparatus according to claim 7, wherein said detecting section and said plurality of slice collimators are moved together relative to the object placed in the measurement space in a direction parallel to the central axis by said moving means.

13. A PET apparatus according to claim 7, wherein said detecting section and said plurality of slice collimators arc reciprocally moved together relative to the object placed in the measurement space in a direction parallel to the central axis by said moving means.

14. A PET apparatus according to claim 7, wherein the relative movement is performed within the measurement space by a distance corresponding to not less than ½ an arrangement pitch of said plurality of cylindrical detectors in the period.

15. A PET apparatus according to claim 14, wherein the distance is an integer multiple of the pitch.

16. A PET apparatus according to claim 7, wherein the relative movement is performed at a constant speed.

17. A PET apparatus according to claim 7, wherein when regions of interest of the object exist over a predetermined range in the central axis direction, each region in the predetermined range stays in the measurement space for a substantially constant period of time during the period.

18. A PET apparatus comprising:
a plurality of photon detection elements which detect one photon and the other photon generated upon electron-positron pair annihilation with light-receiving surfaces facing a measurement space;
a plurality of block detectors which are formed by two-dimensionally arraying said plurality of photon detection elements and arranged in a direction crossing a direction in which the light-receiving surfaces face;
a plurality of collimators which guide only the photons flying from a predetermined direction to said plurality of photon detection elements, respectively;
a coincidence counting information accumulating section which accumulates, when one pair of photon detection elements included in said plurality of block detectors simultaneously detect a photon pair, coincidence counting information of the photon pair detected by said one pair of photon detection elements during a period in which measurement is performed while said plurality of block detectors and said plurality of collimators are relatively moved together; and
an image reconstructing section which reconstructs an image representing a spatial distribution of occurrence frequencies of photon pairs in the measurement space on the basis of the coincidence counting information accumulated by said coincidence counting information accumulating section.

19. A PET apparatus according to claim 18, further comprising moving means for relatively moving said plurality of block detectors and said plurality of collimators together in a direction crossing a direction in which the light-receiving surfaces face.

20. A PET apparatus according to claim 19, wherein said plurality of block detectors and said plurality of collimators are moved together in a direction crossing the direction in which the light-receiving surfaces face.

21. A PET apparatus according to claim 19, wherein
said apparatus further comprises a bed placed in the measurement space, and
said bed is moved by said moving means in a direction crossing the direction in which the light-receiving surfaces face.

* * * * *